United States Patent [19]
Wiedderrecht et al.

[11] Patent Number: 5,457,182
[45] Date of Patent: Oct. 10, 1995

[54] FK-506 CYTOSOLIC BINDING PROTEIN, FKBP12.6

[75] Inventors: Gregory J. Wiederrecht, Westfield; Tonya J. Sewell, Edison, both of N.J.

[73] Assignee: Merck & Co., Inc., Rahway, N.J.

[21] Appl. No.: 197,795

[22] Filed: Feb. 15, 1994

[51] Int. Cl.$^6$ .......................... C07K 14/47; C07K 17/00
[52] U.S. Cl. .................. 530/402; 530/350; 530/413; 435/69.1; 435/7.8; 435/233
[58] Field of Search ................................. 530/350, 402; 435/69.1

[56] References Cited

U.S. PATENT DOCUMENTS 5,109,112   4/1992   Siekierka et al. .

FOREIGN PATENT DOCUMENTS

| | | |
|---|---|---|
| 0293892A2 | 12/1988 | European Pat. Off. . |
| 0481673A2 | 4/1992 | European Pat. Off. . |
| WO91/04321 | 4/1991 | WIPO . |
| WO91/17439 | 11/1991 | WIPO . |
| WO92/01052 | 1/1992 | WIPO . |
| WO92/19745 | 11/1992 | WIPO . |
| WO93/07269 | 4/1993 | WIPO . |
| WO93/23548 | 11/1993 | WIPO . |

OTHER PUBLICATIONS

Rosborough, S. L., et al. (1991) Transplant. Proc. 23(6): 2890–93.
Fischer et al., "Cyclophilin and Peptidyl–prolyl cis–trans Isomerase are Probably Identical Proteins", *Nature*, vol. 337, p. 476 (1989).
A. Galat, "Peptidylproline cis–trans–isomerases: Immunophilins", *Eur. J. Biochem.*, 216, pp. 689–707 (1993).
Harding et al., "A Receptor for the Immunosuppressant FK506 is a cis–trans Peptidyl–prolyl Isomerase", *Nature*, vol. 341, pp. 758 (1989).
Jin et al., "Molecular Cloning of a Membrane–associated Human FK506–and Rapamycin–binding Protein, FKBP–13", *Proc. Natl. Acad. Sci. USA*, vol. 88, pp. 6677–6681 (1991).
Lin et al., "FK–506 and Cyclosporin A Inhibit Highly Similar Signal Transduction Pathways in Human T Lymphocytes", *Cell. Immunol.*, 133, pp. 269–284 (1991).
Liu et al., "Calcineurin is a Common Target of Cyclophilin–Cyclosporin A and FKBP–FK506 Complexes", *Cell*, vol. 66, pp. 807–815 (1991).
Maki et al., "Complementary DNA Encoding . . . Distinct from Cyclophilin", *Proc. Natl. Acad. Sci. USA*, vol. 87, pp. 5440–5443 (1990).
Mozier et al., "Amino Acid Sequence of a 12–kDa Inhibitor of Protein Kinase C", *Eur. J. Biochem.*, 194, pp. 19–23 (1990).
Murthy et al., "Identification of a 14 kDa Immunophilin from Calf Thymus Which Binds to Both Rapamycin and FK–506", *Clin. Chem.*, vol. 39, No. 6, p. 1230 (1993).

O'Keefe et al., "FK–506–and CsA–sensitive Activation of the Interleukin–2 Promoter by Calcineurin", *Nature*, vol. 357, p. 692 (1992).
Pilot–Matias et al., "High–level synthesis of the 12–kDa Human FK506–binding Protein in *Escherichia coli* Using Translational Coupling", *Gene*, 128, pp. 219–225 (1993).
Siekierka et al., "FK–506, a Potent Novel Immunosuppressive Agent, . . . Cyclosporin A–binding Protein, Cyclophilin", *J. Immunol.*, vol. 143, pp. 1580–1583 (1989).
Siekierka et al., "A cytosolic Binding Protein . . . Distinct from Cyclophilin", *Nature*, vol. 341, p. 755 (1989).
Siekierka et al., "The Cytosolic–binding Protein . . . Peptidyl–Prolyl cis–trans Isomerase", *J. Biol. Chem.*, vol. 265, No. 34, pp. 21011–21015 (1990).
Standaert et al., "Molecular Cloning and Overexpression of the Human FK506–binding Protein FKBP", *Nature*, vol. 346, p. 671 (1990).
Takahashi et al., "Peptidyl–prolyl cis–trans Isomerase is the Cyclosporin A–binding Protein Cyclophilin", *Nature*, vol. 337, p. 473 (1989).
Tocci et al., "The Immunosuppressant FK506 Selectively Inhibits Expression of Early T Cell Activation Genes", *J. Immunol.* vol. 143, pp. 718–726 (1989).
Wiederrecht et al., "Isolation of a Human cDNA Encoding a 25 kDA FK–506 and Rapamycin Binding Protein", *Biochem. Biophys. Res. Commun.*, vol. 185, No. 1, pp. 298–303 (1992).
Wiederrecht et al., "Characterization of High Molecular . . . as a Protein Complex", *J. Biol. Chem.*, vol. 267, No. 30, pp. 21753–21760 (1992).
T. J. Sewell, et al., *J. Bio. Chem.*, 269 (33), 21094–21102(Aug. 19, 1994), "Inhibition of Calcineurin by a Novel FK–506–binding Protein".
H. Arakawa et al., "Molecular Cloning and Expression of a Novel Human Gene That is Highly Homologous to Human FK506–Binding Protein 12kDa (hFKBP–12) and Characterization of Two Alternatively Spliced Transcripts," *Biochem. Biophys. Res. Commun.*, 200 (2), pp. 836–843 (Apr. 29, 1994).

*Primary Examiner*—Garnette D. Draper
*Assistant Examiner*—David L. Fitzgerald
*Attorney, Agent, or Firm*—Mollie M. Yang; David L. Rose

[57] ABSTRACT

A new homogeneous cytosolic binding protein (FKBP12.6), having a specific binding activity of about 4.8 mg FK-506 per mg protein and a molecular weight of about 10–12 kilodaltons, reversibly binds the immunosuppressant FK-506, but not cyclosporine A (CSA). The protein is unstable to heating at 56° C. for 30 minutes losing its FK-506 binding affinity. The FKBP12.6 protein is isolated from the cytosol of mammalian tissues, preferably bovine or human brain tissue, and can be used in diagnostic and purification procedures involving FK-506-type macrolide immunosuppressants. The FKBP12.6 protein also has peptidyl-proline isomerase enzymatic activity, catalyzing the cis-trans isomerization of proline-containing peptide bonds. In addition, FKBP12.6 binds to and inhibits the phosphatase calcineurin in the presence of FK-506.

3 Claims, No Drawings

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 103 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:1:

Gly  Val  Glu  Ile  Glu  Thr  Ile  Ser  Pro  Gly  Asp  Gly  Arg  Thr  Phe  Pro

|   | 1 |   |   |   | 5 |   |   |   |   | 10 |   |   |   |   | 15 |   |
|---|---|---|---|---|---|---|---|---|---|----|---|---|---|---|----|---|
|   | Lys | Lys | Gly | Gln | Thr | Cys | Val | Val | His | Tyr | Thr | Gly | Met | Leu | Gln | Asn |
|   |     |     |     | 20  |     |     |     |     | 25  |     |     |     |     | 30  |     |     |
|   | Gly | Lys | Lys | Phe | Asp | Ser | Ser | Arg | Asp | Arg | Asn | Lys | Pro | Phe | Lys | Phe |
|   |     |     | 35  |     |     |     |     | 40  |     |     |     |     | 45  |     |     |     |
|   | Arg | Ile | Gly | Lys | Gln | Glu | Val | Ile | Lys | Gly | Phe | Glu | Glu | Gly | Ala | Ala |
|   |     | 50  |     |     |     |     | 55  |     |     |     |     | 60  |     |     |     |     |
|   | Gln | Met | Ser | Leu | Gly | Gln | Arg | Ala | Lys | Leu | Thr | Cys | Thr | Pro | Asp | Val |
|   | 65  |     |     |     |     | 70  |     |     |     |     | 75  |     |     |     |     | 80  |
|   | Ala | Tyr | Gly | Ala | Thr | Gly | His | Pro | Gly | Val | Ile | Pro | Pro | Asn | Ala | Thr |
|   |     |     |     |     | 85  |     |     |     |     | 90  |     |     |     |     | 95  |     |
|   | Leu | Ile | Phe | Asp | Val | Glu | Leu |   |   |   |   |   |   |   |   |   |
|   |     |     |     |     | 100 |     |     |   |   |   |   |   |   |   |   |   |

( 2 ) INFORMATION FOR SEQ ID NO:2:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

|   | Gly | Val | Gln | Val | Glu | Thr | Ile | Ser | Pro | Gly | Asp | Gly | Arg | Thr | Phe | Pro |
|---|-----|-----|-----|-----|-----|-----|-----|-----|-----|-----|-----|-----|-----|-----|-----|-----|
|   | 1   |     |     |     | 5   |     |     |     |     | 10  |     |     |     |     | 15  |     |
|   | Lys | Arg | Gly | Gln | Thr | Cys | Val | Val | His | Tyr | Thr | Gly | Met | Leu | Glu | Asp |
|   |     |     |     | 20  |     |     |     |     | 25  |     |     |     |     | 30  |     |     |
|   | Gly | Lys | Lys | Phe | Asp | Ser | Ser | Arg | Asp | Arg | Asn | Lys | Pro | Phe | Lys | Phe |
|   |     |     | 35  |     |     |     |     | 40  |     |     |     |     | 45  |     |     |     |
|   | Val | Leu | Gly | Lys | Gln | Glu | Val | Ile | Arg | Gly | Trp | Glu | Glu | Gly | Val | Ala |
|   |     | 50  |     |     |     |     | 55  |     |     |     |     | 60  |     |     |     |     |
|   | Gln | Met | Ser | Val | Gly | Gln | Arg | Ala | Lys | Leu | Thr | Ile | Ser | Pro | Asp | Tyr |
|   | 65  |     |     |     |     | 70  |     |     |     |     | 75  |     |     |     |     | 80  |
|   | Ala | Tyr | Gly | Ala | Thr | Gly | His | Pro | Gly | Ile | Ile | Pro | Pro | Asn | Ala | Thr |
|   |     |     |     |     | 85  |     |     |     |     | 90  |     |     |     |     | 95  |     |
|   | Leu | Ile | Phe | Asp | Val | Glu | Leu | Leu | Lys | Leu | Glu |   |   |   |   |   |
|   |     |     |     |     | 100 |     |     |     |     | 105 |     |   |   |   |   |   |

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:3:

| Asp | Val | Glu | Leu | Leu | Lys | Leu | Glu |
|-----|-----|-----|-----|-----|-----|-----|-----|
| 1   |     |     |     | 5   |     |     |     |

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:4:

```
Gly  Trp  Glu  Glu  Gly  Val  Ala  Gln  Met  Ser  Val
 1              5                        10
```

( 2 ) INFORMATION FOR SEQ ID NO:5:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:5:

```
Ser  Ser  Arg  Asp  Arg  Gln  Lys  Pro  Phe  Lys  Phe
 1              5                        10
```

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

ATGGGNGTNG ARATAGA                                17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

ATGGGNGTNG ARATCGA                                17

( 2 ) INFORMATION FOR SEQ ID NO:8:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

ATGGGNGTNG ARATTGA 17

( 2 ) INFORMATION FOR SEQ ID NO:9:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:9:

CAGCGNATRC CNCGNTG 17

( 2 ) INFORMATION FOR SEQ ID NO:10:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:10:

CAACGNATRC CNCGNTG 17

( 2 ) INFORMATION FOR SEQ ID NO:11:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:11:

CATCGNATRC CNCGNTG 17

( 2 ) INFORMATION FOR SEQ ID NO:12:

( i ) SEQUENCE CHARACTERISTICS:
    ( A ) LENGTH: 17 base pairs

```
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:12:
```

CACCGNATRC CNCGNTG                                                                                17

```
( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:
```

MGNACNTTYC CNAAGAA                                                                                17

```
( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:
```

MGNACNTTYC CNAAAAA                                                                                17

```
( 2 ) INFORMATION FOR SEQ ID NO:15:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:15:
```

AGCTYCTYCC NCGNCG                                                                                 16

```
( 2 ) INFORMATION FOR SEQ ID NO:16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear
```

( i i ) MOLECULE TYPE: cDNA ( i i i ) HYPOTHETICAL: NO ( i v ) ANTI-SENSE: YES ( x i ) SEQUENCE DESCRIPTION: SEQ ID NO:16:

AACTYCTYCC NCGNCG                                                                                               16

( 2 ) INFORMATION FOR SEQ ID NO:17:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

TGGAACCTTG AATTCMGNAC NTTYCCNAAG AA                                                                             32

( 2 ) INFORMATION FOR SEQ ID NO:18:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:18:

AAGCTYCTYC CNCGNCGCCT AGGTTCCAAT GG                                                                             32

( 2 ) INFORMATION FOR SEQ ID NO:19:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:19:

AAACTYCTYC CNCGNCGCCT AGGTTCCAAT GG                                                                             32

( 2 ) INFORMATION FOR SEQ ID NO:20:

( i ) SEQUENCE CHARACTERISTICS:
  ( A ) LENGTH: 120 base pairs
  ( B ) TYPE: nucleic acid
  ( C ) STRANDEDNESS: single
  ( D ) TOPOLOGY: linear ( i i ) MOLECULE TYPE: cDNA (iii) HYPOTHETICAL: NO (iv) ANTI-SENSE: NO (xi) SEQUENCE DESCRIPTION: SEQ ID NO:20:

GGCCAGACGT GCGTGGTGCA CTACACAGGA ATGCTTCAAA ATGGCAAGAA ATTCGATTCA      60

TCCAGAGACA GAAACAAGCC TTTCAAGTTC AGAATTGGCA AACAGGAAGT CATCAAGGGT     120

(2) INFORMATION FOR SEQ ID NO:21:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:21:

GGCCAAACGT GTGTGGTGCA CTACACAGGA ATGCTCCAAA ATGGCAAGAA GTTTGATTCA      60

TCCAGAGACA GAAACAAACC TTTCAAGTTC AGAATTGGCA AACAGGAAGT CATCAAAGGT     120

FK-506 CYTOSOLIC BINDING PROTEIN, FKBP12.6

BACKGROUND OF THE INVENTION

1. Field of the Invention

The present invention relates to a new homogeneous cytosolic binding protein (entitled "FKBP12.6") which binds FK-506 but not cyclosporine A, is unstable to heating at 56° C. for 30 minutes, and has a molecular weight of about 10–12 kilodaltons. The FKBP12.6 protein has peptidyl-proline isomerase enzymatic activity. Moreover, FKBP12.6 binds to and inhibits the phosphatase calcineurin in the presence of FK-506.

2. Brief Description of Disclosures in the Art

Immunoregulatory abnormalities have been shown to exist in a wide variety of "autoimmune" and chronic inflammatory diseases, including systemic lupus erythematosis, chronic rheumatoid arthritis, type 1 diabetes mellitus, type 2 adult onset diabetes, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in pan, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

Cyclosporin A which was approved by the US FDA in 1983 is currently the leading drug used to prevent rejection of transplanted organs. The drug acts by inhibiting the body's immune system from mobilizing its vast arsenal of natural protecting agents to reject the transplant's foreign protein. Although cyclosporin A is effective in fighting transplant rejection, it is nephrotoxic and is known to cause several undesirable side effects including kidney failure, abnormal liver function and gastrointestinal discomfort.

Fujisawa United States, European and Japanese patents and applications (U.S. Pat. No. 4,894,366, EPO Publication No. 0,184,162 and PBJ Disclosure 63-17884) and publications (*J. Am. Chem. Soc.*, 109, 5031 (1987), and *J. Antibiotics*, 40, 1249 (1987)) disclose "FK-506", 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene- 2,3,10,16-tetraone, FR-900506, tacrolimus, which is reputed to be 100 times more potent than cyclosporine. The macrolide is produced by fermentation of a particular strain of *Streptomyces tsukubaensis*.

Extensive clinical studies with FK-506 in the treatment of resistance to organ transplantation have been conducted (see e.g., G. L. Bumgardner, et al., *Gastroenterol. Clin.*, 22 (2), 421–449 (1993)). In addition, FK-506 and related compounds have been suggested to be useful in the treatment of obstructive airways disease, particularly asthma (PCT Publication WO 90/14826), male pattern alopecia or alopecia senilis (EPO Publication No, 0,423,714), rheumatoid arthritis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al., *Lancet,* 1990, 336, 373–74), posterior uveitis (H. Kawashima, *Invest, Ophthalmol. Vis. Sci.*, 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomerulonephritis (J. McCauley, et al., *Lancet*, 1990, 335,674), systemic lupus erythematosus (K. Takabayashi, et al., *Clin. Immunol. Immunopathol.*, 1989, 51, 110–117), multidrag resistance (M. Naito, et al., *Cancer Chemother. Pharmacol.*, 1992, 29, 195–200), inflammation of mucosa and blood vessels (PCT Publication WO 92/17754), cytomegalovirus infection (UK Publication GB 2,247,620A), idiopathic thrombocytopenic purpura and Basedow's disease (PCT Publication WO 91/19495). Also, these compounds are reputed to possess topical activity in the treatment of inflammatory and hyperproliferative skin diseases and cutaneous manifestations of immunologically-mediated illnesses (EPO Pub. No. 0,315, 978).

Although FK-506 has been employed for the treatment of some of the above disorders and diseases, neurological toxicities, which include drowsiness, lethargy, tremors, and aggressiveness (Ohara, K., et al., *Transplant. Proc.*, 22, 83–86 (1990); K. Kumano, et al., *Transplant. Proc.*, 23, 512–515 (1991)), limit its broader use. Accordingly, it would be desirable to understand the mechanism by which FK-506 exerts its immunosuppressive and its toxic effects, as well as develop assays to measure its concentration in biological fluids.

FK-506 shares a number of immunosuppressive properties with cyclosporine A, although it is 10–100 times more potent in this regard. These similarities suggest that both agents may share a similar mechanism of action at the biochemical level (see S. Lin, et al., *Cellular Immunology,* 133,269–284 (1991)). For example, Cyclosporine A is known to bind to the cytosolic protein, cyclophilin (R. E. Handschumacher, et al., *Science*, 226, 544–546 (1984)). The cyclophilin•cyclospofine A complex binds to and inhibits the phosphatase calcineurin (CAN) which is required for T-cell activation and immune system function (S. O'Keefe, et al., *Nature*, 357, 692–694 (1992)). Cyclophilin has also been shown to possess an enzymatic activity, which catalyzes the cis-trans isomerization of peptidyl prolyl bonds (N. Takahashi et al., *Nature*, 337, 473–475; and Fischer et al., *Nature,* 337,476–478).

FK-506 binds to an abundant, cytosolic 11.8 kDa protein termed the FK-506 binding protein (FKBP12) that is expressed universally among tissues and throughout eukaryotic phylogeny (J. Siekierka, et al., *Nature*, 341,755–757 (1989); M. Harding, et al., *Nature*, 341,758–760 (1989); U.S. Pat. No. 5,109,112). Like the cyclophilin.cyclosporin A comples, the FKBP12.FK-506 complex inhibits calcineurin, a calcium-dependent, serine-threonine phosphatase that is a vital component of the signal transduction pathway resulting in early lymphokine gene transcription (J. Liu, et al., *Cell,* 66, 807–815 (1991); J. Friedman, et al., *Cell,* 66, 799–806 (1991); N. Clipstone, et al., *Nature,* 357, 695–697 (1992); S. O'Keefe, et al., *Nature,* 357,692– 694 (1992)). Human FKBP12 has been cloned (N. Maki, et al., *Proc. Natl. Acad. Sci.*, 87, 5440–5443 (1990); R. Standaert, et al., *Nature,* 346, 671–674 (1990); G. Wiederrecht, et al., *J. Biol. Chem.,* 267(21), 753–760 (1992)) and the amino acid sequence of the bovine FKBP12 has been reported (N. Mozier, et al., *Eur. J. Biochem.*, 194, 19–23 (1990); J. Siekierka, et al., *J. Biol. Chem.*, 265, 21011–21015 (1990)).

FKBP12 is not a lymphoid-specific protein, but is widely distributed in tissues and throughout the phyla. The FKBP12 protein is a member of a new class of enzymes, collectively termed peptidylprolyl isomerases (PPIases) which catalyze isomerization between the cis and trans forms of the Xaa-Pro bond in peptides and proteins. Known FK-506 binding proteins (FKBPs) include: FKBP12 (U.S. Pat. No. 5,109,112); FKBP13 (*Proc. Natl. Acad. Sci.*, 88, 6677–6681 (1991)); FKBP25 (G. Wiedderecht, et al., *Biochem. Biophys. Res. Commun.*, 185, 298–303 (1992)); and FKBP52 (G. Wiedderecht, et al., *J. Biol. Chem.*, 267, 21753–21760 (1992) (see generally, A. Galat, *FEBS*, 216, 689–707 (1993)). Their ubiquity and abundance suggest that FKBPs have an important role in cellular physiology, perhaps in accelerating interconversion between rotational conformers of denatured or recently synthesized proteins. Unlike FKBP12, however, the other reported FKBPs do not bind calcineurin when complexed with FK-506. Accordingly, the isolation and identification of other FKBPs would help to delineate the FK-506 mechanism of therapeutic action and toxicity in the cell.

SUMMARY OF THE INVENTION

The present invention is directed to a homogeneous cytosolic binding protein for FK-506 entitled "FKBP12.6". The FKBP12.6 protein has a molecular weight of 10–12 kilodaltons (as determined by gel filtration), is not stable upon heating at 56° C. for 30 minutes and does not bind cyclosporine A (CsA). This newly discovered protein also contrasts with the CsA binding protein, cyclophilin, described in the above-listed references, in which cyclophilin is described as being heat labile and having a molecular weight of 15–17 Kd. Unlike FKBP12, FKBP12.6 is unstable upon heating at 56° C. for 30 minutes. In addition, this protein differs from FKBP12 in its amino acid sequence. Nevertheless, FKBP12.6 is only the second FKBP identified that, in the presence of FK-506, binds and inhibits calcineurin. In accordance with this invention there is provided a homogeneous binding protein FKBP12.6 having a specific binding affinity for FK-506.

Further characteristics of this FKBP12.6 protein are that it has no specific binding affinity for cyclosporine A; has a molecular weight in the range of 10–12 kilodaltons; a specific binding activity of about 4.8 micrograms FK-506 per mg FKBP12.6 protein; is not stable at 56° C. for 30 minutes; and is derived from a variety of sources including, for example, bovine or human brain tissue; and has an enzymatic activity, which catalyzes the cis-trans isomerization of proline-containing peptide bonds.

Bovine FKBP12.6 has the partial N-terminal amino acid sequence (SEQ ID NO: 1):

Gly Val Glu Ile Glu Thr Ile Ser Pro Gly Asp Gly Arg Thr Phe Pro Lys Lys Gly Gln Thr Cys Val Val His Tyr Thr Gly Met Leu Gln Asn Gly Lys Lys Phe Asp Ser Ser Arg Asp Arg Asn Lys Pro Phe Lys Phe Arg Ile Gly Lys Gln Glu Val Ile Lys Gly Phe Glu Glu Gly Ala Ala Gln Met Ser Leu Gly Gln Arg Ala Lys Leu Thr Cys Thr Pro Asp Val Ala Tyr Gly Ala Thr Gly His Pro Gly Val Ile Pro Pro Asn Ala Thr Leu Ile Phe Asp Val Glu Leu.

In contrast, bovine FKBP12 has the amino acid sequence (SEQ ID NO:2):

Gly Val Gln Val Glu Thr Ile Ser Pro Gly Asp Gly Arg Thr Phe Pro Lys Arg Gly Gln Thr Cys Val Val His Tyr Thr Gly Met Leu Glu Asp Gly Lys Lys Phe Asp Ser Ser Arg Asp Arg Asn Lys Pro Phe Lys Phe Val Leu Gly Lys Gln Glu Val Ile Arg Gly Trp Glu Glu Gly Val Ala Gln Met Ser Val Gly Gln Arg Ala Lys Leu Thr Ile Ser Pro Asp Tyr Ala Tyr Gly Ala Thr Gly His Pro Gly Ile Ile Pro Pro Asn Ala Thr Leu Ile Phe Asp Val Glu Leu Leu Lys Leu Glu.

Also provided is the purified complex formed between a biologically useful ligand and the above-described FKBP12.6 protein, wherein said ligand possesses a specific binding affinity for the FKBP12.6 protein. The ligand can be an immunosuppressant, e.g., FK-506 type macrolide, or an antibody to the FKBP12.6 protein.

Further provided is a method of determining the presence or quantity of a biologically useful ligand, eg. FK-506, having an affinity for the above-described FKBP12.6 protein, in a sample, e.g. a body fluid of an immunosuppressed individual on FK-506 therapy or a fermentation broth, which comprises contacting said sample with the FKBP12.6 protein, wherein said FKBP12.6 protein preferably can be immobilized, for example, on a cyanogen bromide activated Sepharose type affinity column.

Furthermore is provided an embodiment of the method to purify a biologically useful ligand wherein said ligand is present in a sample comprising a fermentation broth, a biological fluid, e.g. human blood, or is a chemical entity that is a potential drug, and wherein said ligand is preferably an immunosuppressant, e.g. FK-506, or is an antibody to the FKBP12.6 protein.

In addition, this invention is directed to an isolated and purified DNA molecule encoding the FKBP12.6 protein, expression vectors for the expression of the FKBP12.6 protein in a recombinant host cell comprising the FKBP12.6 encoding DNA, and processes for the expression of the FKBP12.6 protein in a recombinant host cell.

DESCRIPTION OF THE INVENTION AND PREFERRED EMBODIMENTS

The present invention relates to a heat sensitive, low molecular weight cytosolic binding protein FKBP12.6 for the potent immunosuppressive agent FK-506. The FKBP12.6 protein has been isolated and purified from calf brain. Polymerase chain reaction (PCR) techniques have indicated that FKBP 12.6 is also present in human brain tissue. The FKBP12.6 protein appears to be distinct from cyclophilin by a number of criteria including, molecular weight, heat stability, ligand specificity and amino acid sequence. The FKBP12.6 protein differs from the FKBP12 protein by having a unique amino acid sequence. In addition, FKBP12.6 has a decreased abundance in the cytosol, an inability to renature following heat-treatment at the crude extract stage, and what appears to be a non-ubiquitous tissue distribution.

The potent immunosuppressive agent, cyclosporine A (CsA), has found wide clinical use in the prevention of allograft rejection and treatment of graft versus host disease (B. D. Kahan, *Cyclosporin: Biological Activity and Clinical Applications* (Grune & Stratton, Orlando, Fla., 1983). CsA appears to act specifically during T lymphocyte activation by inhibiting the transcription of a limited set of early T-cell activation genes (IL-2, IL-3, IL-4, gamma-IFN, GM-CSF, TNF and c-myc) (J. F. Elliot et al., *Science* 226, 1439 (1984); M. Kronke et al., *Proc. Natl. Acad. Sci. U.S.A.*, 81, 5214 (1984). The macrolide, FK-506, obtained from *Streptomyces tsukubaensis* has been shown to possess very similar, if not identical, immunosuppressive properties both in vivo and in vitro, though being 10–100 times more potent than CsA in this regard (S. Sawada et al., *J. Immunol.*, 139, 1797 (1987)). Studies on the biochemical nature of the immunosuppressive pathway affected by CsA have led to the purification and characterization of a specific CsA binding protein termed, cyclophilin (R. E. Handschumacher et al., *Science*, 226,544 (1984); M. W. Harding et al., *J. Biol. Chem.* 261, 8547 (1986)). Two isoforms of cyclophilin have been isolated which bind CsA with identical affinities and exhibit a structure-function profile consistent with playing a role in immunosuppression. Recently, it has been reported that FK-506 may bind to and function via a cytoplasmic receptor (V. Warty et al., *Transplantation*, 46, p. 453 (1988)).

FK-506 was isolated from a culture of *Streptomyces tsukubaensis* No. 9993. [$^3$H]-dihydro CsA was made by catalytic reduction of the MeBmt double bond in CsA with tritium gas in dimethylformamide solvent using 10% Pd/C catalyst at room temperature, 1 atmosphere pressure, in a shaker apparatus for an hour, followed by purification by reverse phase high pressure liquid chromatography on a Whatman Partisil OD3 column. The specific activity of the obtained [$^3$H]-dihydro CsA was 44 mCi/mg. [$^3$H]-dihydro FK-506 was prepared by catalytic reduction of the allyl double bound in FK-506 by contacting FK-506 in ethyl acetate solvent with tritium gas under 1 atmosphere pressure and room temperature in the presence of 10% Pd/C catalyst for 20 minutes followed by isolating and purifying the material by reverse phase high pressure liquid chromatography to yield the product which had a specific activity of 49 mCi/mg. Dihydro-[$^3$H]FK-506 was a potent inhibitor of IL-2 secretion in JURKAT cells stimulated with phorbol 12-myristate 13-acetate (PMA) and ionomycin, although 5 times less potent than the parent compound.

Identification of a Cross-Reactive Protein in Calf Brain Extracts

Rabbit anti-peptide antibodies were developed against three thyroglobulin-conjugated peptides derived from the human FKBP12 amino acid sequence (Maki, N., et al., *Proc. Natl. Acad. Sci. U.S.A.*, 87, 5440–5443 (1990); Standaert, R., et al., *Nature*, 346, 671–674 (1990)). The three peptides included sequences from the C-terminus (amino acids 100–107) (SEQ ID NO:3):

Asp Val Glu Leu Leu Lys Leu Glu (the "C-terminal peptide"), a sequence spanning the well-conserved tryptophan residue found in most FK-506 binding proteins (amino acids 58–68) (SEQ ID NO:4):

Gly Trp Glu Glu Gly Val Ala Gln Met Ser Val and a sequence spanning amino acids 38 through 48 (SEQ ID NO:5):

Ser Ser Arg Asp Arg Gln Lys Pro Phe Lys Phe

The antibodies were used to survey tissue and cell extracts relevant to either the immunosuppressive effects of FK-506 or to the toxic side-effects of the drug. Accordingly, Western blots were performed using crude extracts prepared from the human T-lymphocytic cell line, Jurkat, rat spleen, rat kidney, and calf brain. FKBP12 is generally well-conserved and so the antisera reacted with FKBP12 in other species. Antisera developed against the C-terminal sequence reacted quite strongly with an additional protein from calf brain that migrates slightly more slowly than authentic bovine FKBP12. From the decreased mobility, we estimate the protein to have a mass of about 12.6 kDa and so we refer to it as FKBP12.6. The antisera did not detect FKBP12.6 in crude extracts from spleen, kidney, or Jurkat extracts indicating that FKBP12.6 may not be as abundant in these tissues. The antisera developed against the other two peptides, while reacting as strongly as the anti-C-terminal peptide sera against FKBP12, reproducibly reacted more weakly with FKBP12.6 in calf brain. Peptide competition experiments demonstrated that the antisera were specific for the C-terminal peptide sequence.

Purification of FKBP12.6 from Calf Brain

The slower mobility of the cross-reactive protein relative to authentic FKBP12 combined with its reduced cross-reactivity with a subset of our antisera suggested that FKBP12.6 might be a novel protein or a modified version of FKBP12 and so a procedure was developed to purify it to homogeneity from a cytosolic extract prepared from calf brain. A heat-treatment step similar to the one used to purify FKBP 12 (Siekierka, J., et al., *Nature*, 341, 755–757 (1989)) resulted in the complete loss of FKBP12.6 and thus was not used. In general, purification of FKBP12.6 was accomplished by the following procedures: (1) obtaining a crude bovine brain extract; (2) CM ion exchange column chromatography (gravity flow); (3) TSK 125 size exclusion HPLC; (4) CM ion exchange chromatography (HPLC); (5) phenyl TSK HPLC; (6) G2000SW size exclusion HPLC; and (7) FK-506 affinity chromatography.

Table I presents a summary of the purification of FKBP12.6.

TABLE I

| | Purification of FKBP12.6 from Calf Brain | | | |
|---|---|---|---|---|
| Step | Volume (ml) | Protein (mg/ml) | FK-506 Binding (ng FK-506 bound/ mg protein) | Total Binding µg FK-506 | Recovery (%) |
| I. S-200 | 2100 | 28.3 | 9.86$^a$ | 586$^a$ | — |
| II. CM-650M | 228 | 15.4 | 1.49 | 5.23 | 100 |
| III. TSK-125 HPLC | 51.7 | 14.4 | 4.23 | 3.15 | 60 |
| IV. CM-3SW HPLC | 24 | 6.8 | 13.3 | 2.17 | 41 |
| V. Phenyl-5PW HPLC | 42 | 0.59 | 52.85 | 1.31 | 25 |
| VI. G2000SW HPLC | 7.3 | 0.12 | 1278.3 | 1.12 | 21 |
| VII. FK-506 Affinity | 2.0 | 0.023 | 4874.0 | 0.224 | 4.3 |

$^a$Activity in the S-200 measures both FKBP12 and FKBP12.6 binding as determined using the LH-20 assay.

The specific activity of binding FK-506 by FKBP12.6 cannot be determined at the S200 stage because of large amounts of authentic FKBP12 in that relatively crude extract. However, FKBP12.6 is separated completely from authentic FKBP12 in Step II by chromatography on the CM-450M column. FKBP12.6 remains bound to the CM column while FKBP12 flows through during loading and washing. FKBP12.6 elutes from the column between 100 and 200 mM NaCl and Westerns of the gradient fractions using the anti-C-terminal peptide antibody confirm that there is no trace of FKBP12 present in the FKBP12.6 fractions. Because of the presence of FKBP12 in the S200, the recovery of FKBP12.6 may only be calculated from the CM-450M step forward using the standard LH-20 binding assay (Handschumacher, R., et al., *Science.* 226, 544–547 (1984)).

Starting with approximately 60 grams of protein in the crude cytosolic brain extract, a typical yield after purification is about 50 μg of homogeneous FKBP12.6 (see Table I). The final step in the purification is binding of the protein to an FK-506 affinity resin. FKBP12.6 was eluted from the resin with 4M guanidine-HCl and renatured by dialysis. The most highly purified material shows a single band on a 16% SDS-PAGE gel and a single peak on an ABI C4 reverse-phase column. The renatured material retains binding to FK-506. Purified FKBP12.6 has a specific binding activity of 4.8 μg of [$^3$H]dihydroFK-506 per mg of protein. This calculates to a 3,271-fold purification from the CM-450M step. Because the CM-450M step removes 94% of the protein from the crude extract, the overall s purification from the S200 is actually much greater. In calf brain cytosol then, FKBP12.6 is clearly much less abundant than FKBP12 is in calf thymus which was purified from that tissue 337-fold to homogeneity with almost the identical recovery (Siekierka, J., et al., *Nature,* 341, 755–757 (1989)). Assuming a mass of 12.6 kDa for FKBP12.6 and a binding stoichiometry of 1 mole of FK-506 per mole of protein, the theoretical specific binding activity is 64 mg of [$^3$H]dihydroFK-506 (molecular weight=805 g/mol) per mg of protein. There is ample precedent for lower than expected binding of [$^3$H]dihydroFK-506 to the FKBPs (Siekierka, J., et al., *Nature,* 341, 755–757 (1989); Wiederrecht, G., et al., *J. Biol. Chem.,* 267, 21753–21760 (1992)). One explanation for the lower than expected specific binding activity is that the Bradford assay used to estimate the protein concentration is known to overestimate both FKBP and cyclophilin concentration when compared to methods such as amino acid analysis (Siekierka, J., et al., *Nature,* 341, 755–757 (1989); Harding, M., et al., *J. Biol. Chem.,* 261, 8547–8555 (1986)). A second explanation for the lower than expected binding is that the LH-20 assay used to estimate binding is not an equilibrium binding assay and ligand off-rates will result in lower calculated specific binding activities. A third explanation is that all of the FKBP12.6 may not be unfolded properly and the unfolded protein may not bind effectively.

Binding of [$^3$H]dihydroFK-506 to FKBP12.6 demonstrates saturation and is of high affinity. Replotting the direct binding data using the Scatchard format yields a Kd value of 0.55 nM. This value is similar to that determined for the binding of [$^3$H]dihydroFK-506 to FKBP12 which was measured to be 0.4 by direct binding.

FKBP12.6 has PPIase activity that is inhibited by FK-506 and rapamycin. Because the renatured material did not have PPIase activity, the PPIase assay was performed using partially purified FKBP12.6 from the previous step in the purification (Step VI). The substrate was N-succinyl-Ala-Leu-Pro-Phe-p-nitroanilide, the preferred peptide substrate of FKBP12 (Harrison, R., et al., *Biochemistry,* 29, 3813–3816 (1990)). FKBP12.6 is about 25% pure at this stage (see Table I, Compare the specific binding activities of the step VI and Step VII material.) and Western analysis demonstrated that no other known FKBPs were present at this point in the purification. The material from step VI did have PPIase activity indicating that while FK-506 binding activity could be regained after renaturation, PPIase activity could not be. The PPIase activity of partially pure FKBP12.6 was compared to that of homogeneous FKBP12 showing that the rate, k(sec$^{-1}$), increases as a function of enzyme concentration. The slope of the FKBP 12 rate is 4.1 fold greater than the slope of the FKBP12.6 rate. When the 25% purity of FKBP12.6 is factored in, it has PPIase activity virtually equivalent to that of FKBP12. Both rapamycin and FK-506 are potent inhibitors of the PPIase activity of FKBP12.6 with rapamycin being a somewhat better inhibitor than FK-506. Assuming that the drugs and peptide bind to the same site as they do in FKBP12, this result suggests that rapamycin has a somewhat greater affinity for FKBP12.6 than does FK-506. The large amount of protein used in the PPIase assay (400 nM) precludes a comparison of the IC50s required to inhibit FKBP12.6 with the Kd value for FK-506 described above. However, the assay is valid for comparing drug affinities.

The FKBP12.6.FK-506 complex binds calcineurin. An HPLC size-exclusion radiochromatographic assay that monitors complex formation between FKBP12.FK-506 and CaN has been described previously (Wiederrecht, G., et al., *J. Biol. Chem.,* 267, 21753–21760 (1992)). In that assay, the FKBP12.FK-506 complex elutes from an analytical sizing column (SEC400) in later fractions. When CaN and CaM are added, a higher molecular weight FKBP12.FK-506.CaN-.CaM complex forms which elutes in earlier fractions well-separated from the FKBP.FK-506 complex. A modification of that assay was used to show that FKBP12.6 binds CaN in the presence of FK-506. In the modified assay, samples were assayed by Western analysis using the anti-C-terminal peptide antibody in order to identify FKBP12 and FKBP12.6 in various chromatographic fractions.

In the first experiment, FKBP12 and FKBP12.6 were partially purified by preparative HPLC gel filtration chromatography on a Bio-Sil TSK-125 column. These partially purified FKBPs (containing both FKBP12 and FKBP12.6) are devoid of CaN which separates completely from them on this column. FKBP12 and FKBP12.6 co-elute at fractions 26 and 27 on the analytical sizing column (G2000SW) used in this experiment. First, a "positive-control" experiment using the crude CaN-depleted FKBPs was performed to confirm that Western analysis could substitute for the radiochromatographic analysis and detect the shift of FKBP12 to higher molecular weight fractions when CaN, CaM, Ca$^{2+}$, Mg$^{2+}$, and FK-506 are added exogenously. As expected, in the presence of exogenous CaN a significant fraction of FKBP12 is in the FKBP12.FK-506-CaN complex found in the higher molecular weight fractions (#'s 20–23) and some uncomplexed FKBP12 remains in fractions 26 and 27, thereby validating the assay. Because this crude FKBP material also contains FKBP12.6, it can also be observed migrating slightly above FKBP12 in FIG. 4A. Most of the FKBP12.6 is shifted to a high molecular weight complex in the presence of CaN, CaM, Ca$^{2+}$, Mg$^{2+}$, and FK-506.

To more carefully examine the requirements for FKBP12.6 complex formation with CaN, experiments were conducted using purified FKBP12.6. As described above, in the absence of CaN the FKBP12.6.FK-506 complex elutes from the sizing column at fractions 26 and 27. When FKBP12.6 is incubated with CaN, CaM, and Ca$^{2+}$, Mg$^{2+}$ (but without FK-506) and the mixture is assayed in the column assay, FKBP12.6 continues to elute at fractions 26 and 27. However, when FKBP12.6 is incubated with CaN, CaM, $Ca^{2+}$, $Mg^{2+}$ and FK-506 and the mixture is assayed, all of the immunoreactive FKBP12.6 is shifted to fractions (20–22) demonstrating that FKBP12.6 has formed a complex with CaN. Like FKBP12, FKBP12.6 complex formation with CaN occurs only in the presence of the drug FK-506.

To further confirm our observation that FKBP12.6 binds to CaN, it was tested for its ability to inhibit calcineurin phosphatase activity in the presence of FK-506. The FKBP12.6 material used in the experiment was homogeneous material purified through the FK-506 affinity column step (Step VII) and renatured. For a side-by-side comparison, FKBP12 was also tested for its ability to inhibit calcineurin in the presence of drug. The FKBP12 protein used was purified to homogeneity from bacteria over-expressing recombinant human FKBP12 (Wiederrecht, G., et al., *J. Biol. Chem.*, 267, 21753–21760 (1992). Increasing concentrations of FKBP12.6 and FKBP12 were added to a cocktail containing FK-506, CaN, CaM, $Ca^{2+}$, and $Mg^{2+}$. FIG. 5 shows that FKBP12.6 is almost equipotent to FKBP12 in its ability to block CaN phosphatase activity. The IC50's for inhibition of CaN are 16.0 nM and 9.9 nM for FKBP12.6 and FKBP12, respectively.

FKBP12.6 is not N-terminally blocked and so it was possible to obtain N-terminal amino acid sequence by Edman degradation. Deduction from sequencing of peptides derived from proteolytic digestion and cyanogen bromide (CNBr) cleavage of FKBP12.6 gave the partial N-terminal amino acid sequence (SEQ ID NO: 1) depicted below:

Gly Val Glu Ile Glu Thr Ile Ser Pro Gly Asp Gly Arg Thr Phe Pro Lys Lys Gly Gln Thr Cys Val Val His Tyr Thr Gly Met Leu Gln Asn Gly Lys Lys Phe Asp Ser Ser Arg Asp Arg Asn Lys Pro Phe Lys Phe Arg Ile Gly Lys Gln Glu Val Ile Lys Gly Phe Glu Glu Gly Ala Ala Gln Met Ser Leu Gly Gln Arg Ala Lys Leu Thr Cys Thr Pro Asp Val Ala Tyr Gly Ala Thr Gly His Pro Gly Val Ile Pro Pro Asn Ala Thr Leu Ile Phe Asp Val Glu Leu

With the exception of the C-terminal 31 amino acids shown, the sequence of the peptide products and of the N-terminus was confirmed two to three times. Alignment with bovine FKBP12 (Harding, M., et al., *Nature*, 341, 758–760 (1989); Siekierka, J., et al., *J. Biol. Chem.*, 265, 21011–21015 (1990); Mozier, N., et al., *Eur. J. Biochem.*, 194, 19–23 (1990)) shows that FKBP12.6 is highly similar to FKBP12 having about 84% amino acid identity overall with most of the differences between the two sequences being very conserved changes.

The only non-conserved changes detected thus far are a Val to Arg substitution at position 49, a Trp to Phe substitution at position 59, a Val to Ala substitution at position 63, a Tyr to Val substitution at position 80, and an Ile to Cys change at position 76. The unique amino acid sequence indicates that FKBP12.6 is a novel gene product and not a post-translationally modified version of FKBP12. Taking advantage of the few amino acid differences between FKBP12 and FKBP12.6, nested PCR has been performed successfully using bovine brain cDNA as a template to obtain a nucleic acid probe encoding a portion of the open reading frame (ORF). Translation of that PCR product, which encodes residues G19 through G58 has confirmed the amino acid sequence information within that region.

Utility and Application of the FKBP12.6 Protein

The FKBP12.6 protein, per se or immobilized, can be used as a specific binding partner to a variety of binding ligands for diagnostic, purification or investigatory procedures. A preferred immobilizing matrix is cyanogen bromide activated Sepharose (Phamacia) to which the FKBP12.6 protein can be covalently linked, forming an affinity chromatography column.

The FKBP12.6 protein is of physiological importance because of the high specificity for binding active forms of the immunosuppressant, FK-506. The above described immobilized affinity matrix can be prepared which reversibly binds FK-506 in a complex, which can be eluted with aqueous buffer reagents of increasing ionic strength. The formed affinity matrix can also be used to detect FK-506-like macrolide substances by displacement of tritiated ($^3$H)-FK-506. These compounds include FK-520, FK-523, FK-525 and other FK-506 analogs as disclosed in EPO Publication No. 0,184,162.

The matrix also provides a method to identify and/or quantify FK-506 in serum and other body fluids as well as detect FK-506 like cellular constituents which may be natural ligands.

Still further, the matrix is useful in screening candidate chemical structures that, like FK-506, can have immunosuppressive activity and, therefore, is useful in the development of other classes of drugs that function through the action of this protein.

Since the FKBP12.6 protein has been purified to homogeneity, oligonucleotide probes can be used to identify the gene thereby allowing the protein to be produced by known recombinant DNA techniques. A typical procedure for the purification of the FKBP12.6 protein is described in the following examples.

Since, the FKBP12.6 protein has an affinity for the immunosuppressant FK-506, and its active analogs, it or certain derived chemicals and/or natural derivatives thereof, including subfragments of the whole protein, can be used as a specific binding partner for these ligands in numerous receptor binding procedures known in the art.

Similarly, it can be used to purify a desired ligand from a composition containing ligand. For example, the FKBP12.6 protein can be used for purifying FK-506 or related structures from a yeast fermentation broth in which the FK-506 is produced. Further, it can be used to select compounds which bind to the FKBP12.6 protein as a screening test for identifying new immunosuppressant drugs. In these various procedures, it is preferred, although not required, to immobilize the FKBP12.6 protein. This can be accomplished by any procedure known in the art. A particularly useful support for immobilizing proteins is cyanogen bromide treated Sepharose (CNBR-activated Sepharose 4B, Pharmacia, Piscataway, N.J.). The immobilized FKBP12.6 protein is prepared by mixing the protein under basic conditions with the cyanogen bromide-activated Sepharose. The binding of the FKBP12.6 protein to this matrix can result in a marked stabilization of the bound activity through a three-dimensional stabilization achieved by multiple bonds through the amino groups of the FKBP 12.6 protein.

The preferred immobilized FKBP12.6 protein can also be used diagnostically for the determination of the concentration of FK-506 and its metabolites from physiological fluids, e.g. body fluids, and tissue extracts as for example in patients who are undergoing FK-506 immunosuppressive therapy.

The protein can also be used in an assay to bind FK-506 type macrolide compounds and biologically useful ligands, by allowing the FKBP12.6 protein and FK-506 type macrolide/ligand to form a complex in an excess of the macrolide, then eluding the mixture through a column and analyzing the concentration of the pure complex spectrophotometrically or by scintillation counting. By this methodology, pure samples of the complex can be formed, from which the macrolide or biologically useful ligand can be isolated by interrupting the binding with an e.g. strong ionic salt solution and followed by conventional chromatographic separation.

Cloning and Expression of FKBP12.6 Protein

Any of a variety of procedures may be used to clone FKBP12.6 cDNA. These methods include, but are not limited to, direct functional expression of the FKBP12.6 cDNA following the construction of an FKBP12.6-containing cDNA library in an appropriate expression vector system. Another method is to screen an FKBP12.6-containing cDNA library constructed in a bacteriophage or plasmid shuttle vector with a labelled oligonucleotide probe designed from the amino acid sequence of the FKBP12.6 protein. The preferred method consists of screening an FKBP12.6-containing cDNA library constructed in a bacteriophage or plasmid shuttle vector with a partial cDNA encoding the FKBP12.6 protein. This partial cDNA is obtained by the specific PCR amplification of FKBP12.6 DNA fragments through the design of degenerate oligonucleotide primers from the amino acid sequence known for other FK-506 binding proteins.

It is readily apparent to those skilled in the art that other types of libraries, as well as libraries constructed from other cells or cell types, may be useful for isolating FKBP12.6 encoding DNA. Other types of libraries include, but are not limited to, cDNA libraries derived from other cells or cell lines other than bovine or human brain cells, and genomic DNA libraries.

It is readily apparent to those skilled in the art that suitable cDNA libraries may be prepared from cells or cell lines which have FKBP12.6 activity. The selection of cells or cell lines for use in preparing a cDNA library to isolate FKBP12.6 cDNA may be done by first measuring cell associated FKBP12.6 activity using the known labelled ligand binding assay cited above and used herein.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982).

It is also readily apparent to those skilled in the art that DNA encoding FKBP12.6 may also be isolated from a suitable genomic DNA library.

Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manuel (Cold Spring Harbor Laboratory, Cold Spring Harbor, N.Y., 1982).

In order to clone the FKBP12.6 gene by one of the preferred methods, the amino acid sequence or DNA sequence of FKBP12.6 or a homologous protein is necessary. To accomplish this, FKBP12.6 protein or a homologous protein may be purified and its partial amino acid sequence determined by automated sequencers. It is s not necessary to determine the entire amino acid sequence, but the linear sequence of two regions of 6 to 8 amino acids can be determined for the PCR amplification of a partial FKBP12.6 DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the FKBP12.6 sequence but others in the set will be capable of hybridizing to FKBP12.6 DNA even s in the presence of DNA oligonucleotides with mismatches. The mismatched DNA oligonucleotides may still sufficiently hybridize to the FKBP12.6 DNA to permit identification and isolation of FKBP12.6 encoding DNA.

Using one of the preferred methods, cDNA clones encoding FKBP12.6 are isolated in a two-stage approach employing polymerase chain reaction (PCR) based technology and cDNA library screening. In the first stage, $NH_2$-terminal and internal amino acid sequence information from the purified FKBP12.6 or a homologous protein is used to design degenerate oligonucleotide primers for the amplification of FKBP12.6-specific DNA fragments. In the second stage, these fragments are cloned to serve as probes for the isolation of full length cDNA from a cDNA library derived from bovine or from human brain cells.

The sequence for the partial cDNA encoding bovine FKBP12.6 is depicted below (SEQ ID NO:20):

```
5'-GGC CAG ACG TGC GTG GTG CAC TAC ACA GGA ATG
CTT CAA AAT GGC AAG AAA TTC GAT TCA TCC AGA
GAC AGA AAC AAG CCT TTC AAG TTC AGA ATT GGC
AAA CAG GAA GTC ATC AAG GGT-3'
```

The sequence for the partial cDNA encoding human FKBP12.6 is depicted below (SEQ ID NO:21):

```
5'-GGC CAA ACG TGT GTG GTG CAC TAC ACA GGA ATG
CTC CAA AAT GGC AAG AAG TTT GAT TCA TCC AGA
GAC AGA AAC AAA CCT TTC AAG TTC AGA ATT GGC
AAA CAG GAA GTC ATC AAA GGT-3'
```

As will be clear to one skilled in the art, due to degeneracy, the sequence of the DNA molecule encoding bovine FKBP12.6 is different from the sequence of the DNA molecule encoding human FKBP12.6.

The cloned FKBP12.6 cDNA obtained through the methods described above may be recombinantly expressed by molecular cloning into an expression vector containing a suitable promoter and other appropriate transcription regulatory elements, and transferred into prokaryotic or eukaryotic host cells to produce recombinant FKBP12.6. Techniques for such manipulations can be found described in Maniatis, T, et al., supra, and are well known in the art.

Expression vectors are defined herein as DNA sequences that are required for the transcription of cloned DNA and the translation of their mRNAs in an appropriate host. Such vectors can be used to express eukaryotic DNA in a variety of hosts such as bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant FKBP12.6 in mammalian cells. Commercially available mammalian expression vectors which may be suitable for recombinant FKBP12.6 expression, include but are not limited to, pMC1neo (Stratagene), pXT1 (Stratagene), pSG5 (Stratagene), pcDNAI, pcDNAI-amp (Invitrogen), EBO-pSV2-neo (ATCC 37593) pBPV-I(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565)

DNA encoding FKBP12.6 may also be cloned into an expression vector for expression in a host cell. Host cells may be prokaryotic or eukaryotic, including but not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC5 (ATCC CCL 171).

The expression vector may be introduced into host cells via any one of a number of techniques including but not limited to transformation, transfection, protoplast fusion, and electroporation. The expression vector-containing cells are individually analyzed to determine whether they produce FKBP12.6 protein. Identification of FKBP12.6 expressing cells may be done by several means, including but not limited to immunological reactivity with anti-FKBP12.6 antibodies, and the presence of host cell-associated FKBP12.6 activity.

Expression of FKBP12.6 DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes s being preferred.

To determine the FKBP12.6 cDNA sequence(s) that yields optimal levels of FKBP12.6 protein, FKBP12.6 cDNA molecules including but not limited to the following can be constructed: the full-length open reading frame of the FKBP12.6 cDNA and various constructs containing portions of the cDNA encoding only specific domains of the receptor protein or rearranged domains of the protein. All constructs can be designed to contain none, all or portions of the 5' and/or 3' untranslated region of FKBP12.6 cDNA. FKBP12.6 activity and levels of protein expression can be determined following the introduction, both singly and in combination, of these constructs into appropriate host cells. Following determination of the FKBP12.6 cDNA cassette yielding optimal expression in transient assays, this FKBP12.6 cDNA construct is transferred to a variety of expression vectors (including recombinant viruses), including but not limited to those for mammalian cells, plant cells, insect cells, oocytes, E. coli, and yeast cells.

Mammalian cell transfectants are analyzed for both the levels of FKBP12.6 activity and levels of FKBP12.6 protein by the following methods. Assessing FKBP12.6 activity involves the direct introduction of a labelled ligand to the cells and determining the amount of specific binding of the ligand to the FKBP12.6-expressing cells. Binding assays for receptor activity are known in the art (Frey et al., Eur. J. Pharmacol., 244, 239–250 (1993)).

Levels of FKBP12.6 protein in host cells is quantitated by a variety of techniques including, but not limited to, immunoaffinity and/or ligand affinity techniques. FKBP12.6-specific affinity beads or FKBP12.6-specific antibodies are used to isolate $^{35}$S-methionine labelled or unlabelled FKBP12.6 protein. Labelled FKBP12.6 protein is analyzed by SDS-PAGE. Unlabelled FKBP12.6 protein is detected by Western blotting, ELISA or RIA assays employing FKBP12.6 specific antibodies.

Following expression of FKBP12.6 in a host cell, FKBP12.6 protein may be recovered to provide FKBP12.6 in active form, capable of binding FKBP12.6-specific ligands. Several FKBP12.6 purification procedures are available and suitable for use. Recombinant FKBP12.6 may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant FKBP12.6 can be separated from other cellular proteins by use of an immuno-affinity column made with monoclonal or polyclonal antibodies specific for full length nascent FKBP12.6, or polypeptide fragments of FKBP12.6.

Monospecific antibodies to FKBP12.6 are purified from mammalian antisera containing antibodies reactive against FKBP12.6 or are prepared as monoclonal antibodies reactive with FKBP12.6 using the technique of Kohler and Milstein, Nature 256:495–497 (1975). Monospecific antibody as used herein is defined as a single antibody species or multiple antibody species with homogenous binding characteristics for FKBP12.6. Homogenous binding as used herein refers to the ability of the antibody species to bind to a specific antigen or epitope, such as those associated with the FKBP12.6, as described above. FKBP12.6 specific antibodies are raised by immunizing animals such as mice, rats, guinea pigs, rabbits, goats, horses and the like, with an appropriate concentration of FKBP12.6 either with or without an immune adjuvant.

Preimmune serum is collected prior to the first immunization. Each animal receives between about 0.1 µg and about 1000 µg of FKBP12.6 associated with an acceptable immune adjuvant. Such acceptable adjuvants include, but are not limited to, Freund's complete, Freund's incomplete, alum-precipitate, water in oil emulsion containing Corynebacterium parvum and tRNA. The initial immunization consisted of the enzyme in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of FKBP12.6 in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with FKBP12.6 are prepared by immunizing inbred mice, preferably Balb/c, with FKBP 12.6. The mice are immunized by the IP or SC route with about 1 µg to about 100 µg, preferably about 10 µg, of FKBP12.6 in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 µg of FKBP12.6 in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using FKBP12.6 as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-FKBP12.6 mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of FKBP12.6 in body fluids or tissue and cell extracts.

It is readily apparent to those skilled in the art that the above described methods for producing monospecific antibodies may be utilized to produce antibodies specific for FKBP12.6 polypeptide fragments, or full-length FKBP12.6 polypeptide.

FKBP12.6 antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) and the cell culture supernatants or cell extracts containing FKBP12.6 or FKBP12.6 fragments are slowly passed through the column. The column is then washed with phosphate buffered saline until the optical density falls to background, then the protein is eluted with 0.23M glycine-HCl (pH 2.6). The purified FKBP12.6 protein is then dialyzed against phosphate buffered saline.

One method suitable for the isolation of DNA encoding the FKBP12.6 receptor of the present invention involves the utilization of amino acid and/or DNA sequence information obtained from other FK- 506 binding proteins. Since FK-506 binding proteins are classified together, certain regions or domains such as the transmembrane and/or cytoplasmic domains, are expected to have some degree of homology sufficient to produce a probe for the isolation of novel proteins.

Various changes and modifications may be made in the products and processes of the present invention without departing from the spirit and scope thereof. The various embodiments and the examples which have been set forth herein are given for the purpose of illustrating the present invention and shall not be construed as being limitations on the scope or spirit of the instant invention.

EXAMPLE 1

Preparation of Calf Brain Cytosol

Twelve calf brains were homogenized in 2.4 liters of buffer containing 5 mM sodium phosphate (pH 6.8), 1 mM EDTA, 5 mM 2-mercaptoethanol, and 1 mM PMSF. Homogenization was performed for 3 min at 4° C. in a Waring blender. 500 ml portions of the blender homogenate were subjected to further homogenization at 4° C. with three 30 sec bursts of a Polytron apparatus set at the maximum speed. The homogenate was subjected to centrifugation (10,000 rpm for 15 min) in a JA-10 rotor. The homogenate was further clarified by centrifugation (40,000 rpm for 1 hr) in a Ti45 rotor. The homogenate was dialyzed for 24 hrs against 28 liters of homogenization buffer not containing PMSF.

EXAMPLE 2

Purification of the Novel FKBP from Calf Brain

The dialyzed homogenate was applied to a column (5 cm× 30 cm) of TosoHaas CM-650M resin equilibrated in 5 mM sodium phosphate (pH 6.8), 1 mM EDTA, and 5 mM 2-mercaptoethanol (CM Buffer). The column was subsequently washed with six column volumes of CM buffer. Bound protein was eluted with a linear gradient s (total volume, 2 liters) of 0–1M NaCl in CM buffer. Fractions (21 ml) were collected at a flow rate of 125 ml/hr. FK-506 binding activity eluted between 100 and 200 mM NaCl. Active fractions were combined, concentrated to 50 ml in an Amicon stirred pressure cell containing a YM3 filtration membrane. 4.5 ml of the concentrated protein were applied per injection to a Bio-Sil TSK-125 gel filtration HPLC column (21.5 mm×60 cm, Bio-Rad) equipped with a SW guard column (21.5 mm×7.5 cm). Protein was eluted at a flow rate of 4 ml/min in buffer containing 100 mM sodium phosphate (pH 6.8), 50 mM $Na_2SO_4$, 5 mM 2-mercaptoethanol, and 1 mM EDTA (TSK Buffer). Fractions (3 ml) were collected and activity eluted between fractions 52 and 59. The active fractions from the ten to fifteen HPLC gel filtration runs were combined, concentrated to about 40 ml in an Amicon stirred cell, and dialyzed overnight against CM buffer. 4.5 ml of the concentrated protein were applied per injection to a TosoHaas CM-3SW HPLC column (21.5 mm×15 cm) at a flow rate of 6 ml/min in CM buffer until all of the protein had been loaded. Protein was eluted with a linear 1 hour gradient of 0–300 mM NaCl in CM buffer. Fractions (6 ml) were collected at a flow rate of 6 ml/min and activity eluted between 100 and 150 mM NaCl. Active fractions were combined, concentrated to about 25 ml using an Amicon stirred cell, and dialyzed overnight against buffer containing 100 mM sodium phosphate (pH 7.0), 0.9M $(NH_4)_2SO_4$, and 5 mM 2-mercaptoethanol.

The protein was applied in 4.5 ml injections (until all of the protein was loaded) to a TosoHaas Phenyl-5PW HPLC column (21.5 mm×15 cm) at a flow rate of 3 ml/min in the dialysis buffer. Protein was eluted in a linear 45 minute gradient beginning with 100 mM sodium phosphate (pH 7.0) and 0.9M $(NH_4)_2SO_4$ and ending with CM buffer. The flow rate was 3 ml/min and 1 min fractions were collected. FK-506 binding activity eluted between 300 and 60 mM $(NH_4)_2SO_4$. The fractions were combined, concentrated to 2 ml in the Amicon stirred cell, and applied to a TosoHaas G2000SW gel filtration HPLC column (7.5 mm×60 cm). Protein was eluted at a flow rate of 1 ml/min in TSK buffer. 0.5 ml fractions were collected and FK-506 binding activity eluted between fractions 42 and 49. The novel FKBP is about 25% pure at this point. The active fractions were combined incubated with 100 ml of FK-506 affinity resin prepared as described (Harding, M., et al., *Nature*, 341, 758–760 (1989)). After washing, the FK-506 binding activity was eluted by boiling in 1 ml of 4M guanidine-HCl. The protein was then dialyzed overnight in buffer containing 5 mM sodium phosphate (pH 6.8) and 5 mM 2-mercaptoethanol.

EXAMPLE 3

[$^3$H]DihydroFK-506 Binding to FKBP12.6

The basic LH-20 binding assay was performed as described by Handschumacher, R., et al., *Science*, 226, 544–547 (1984) with the modifications noted in Siekierka, J., et al., *Nature*, 341, 755–757 (1989).

EXAMPLE 4

Peptidyl-Prolyl cis-trans Isomerase Assay

PPIase assays were performed as described (Fischer, G., et al., *Nature*, 337,476–478 (1989)) with the following changes: the peptide substrate used was N-succinyl-Ala-Leu-Pro-Phe-p-nitroanilide (BACHEM, California) at a final concentration of 72 µM and chymotrypsin (Sigma) was present in the assay at a concentration of 6 µM. The total reaction volume was 1.5 ml. The release of p-nitroanilide by chymotrypsin was measured by following the increase in absorbance at 405 nm on a Beckman DU68 spectrophotometer. After an initial rapid rise in absorbance due to hydrolysis of the trans peptide, the slow secondary increase in absorbance which reflects the cis-to-trans conversion of the peptide by the PPIase was measured at 3-sec intervals out to 1.5 min. The data were fitted to a simple first-order rate equation and the first-order rate constant, k ($s^{-1}$), calculated.

The FKBP12.6 protein exhibits a low, but significant PPIase activity. The increase in isomerization rate is proportional to the concentration of FKBP12.6 protein. Cyclophilin PPIase activity is approximately 25 fold higher than that of the FKBP12.6 protein. The reason for the differences in activity may reflect substrate specificity or reaction conditions.

The data presented demonstrates that the FKBP12.6 protein, like cyclophilin and FKBP12, has been discovered to possess peptidyl-proline isomerase activity. Although the activity associated with the FKBP12.6 protein is significantly less than that of cyclophilin, it is specifically inhibited by FK-506 and not CsA, suggesting that it does not represent cyclophilin contamination. The association of PPIase activity with both cyclophilin and the FKBP12.6 protein implies that this activity is important during T-cell activation. Furthermore, screening assays can be devised using the assay described above, by one skilled in the art, to identify specific inhibitors which are novel immunosuppressive agents.

EXAMPLE 5

Western Blots

Twenty µg of crude extracts prepared from the cytosols of calf brain, rat kidney, rat spleen, and Jurkat cells were subjected to denaturing electrophoresis on 16% Tris-Glycine gels from Novex. Proteins were transferred at 4° C. to a 0.45 µm Immobilon-P transfer membrane (Millipore) in a Mini Trans-Blot Cell (Bio-Rad) at 150 volts for 90 min. The membrane was blocked overnight at 4° C. on a rocker platform in buffer containing 10% Carnation non-fat dry milk, 0.9% NaCl, 10 mM Tris (pH 7.5), and 0.2% $NAN_3$. The membrane was washed twice in Tris-buffered-saline (TBS) for a total of 10 min. The membrane was incubated for 2 hr at room temperature in 30 ml of buffer containing TBS-0.5% Tween (TBST), 20% heat-inactivated fetal bovine serum, 0.04% $NaN_3$ and the rabbit anti-peptide antiserum diluted 1:10,000. The membrane was washed three times (10 min per wash) in TBST at room temperature. The membrane was incubated for 1 hr at room temperature in TBST containing HRP-conjugated donkeys anti-rabbit secondary antibody (Amersham) diluted 1:10,000. The membrane was washed in TBST for 15 min at room temperature, then more three times (5 min each wash) in TBST, and the membrane was developed using the ECL Western blotting detection system (Amersham).

EXAMPLE 6

FKBP•FK-506•CaN Complex-Formation Assay

Incubations (total volume, 500 µl) were performed for 15 min at 30° C. and contained various combinations of the following components: 38 µg bovine calcineurin, 8 µg bovine calmodulin, 5 µg purified FKBP12.6 which is devoid of FKBP12 or 40 µg of calcineurin-depleted bovine brain extract (which contains both FKBP12 and FKBP12.6), and 3.2 µg FK-506. The incubation buffer contained 20 mM Tris (pH 7.5), 100 mM NaCl, 6 mM $MgCl_2$, 0.1 mM $CaCl_2$, 0.1 mg/ml BSA, and 0.5 mM dithiothreitol. The incubation reaction was chromatographed on a Bio-Sil SEC400 HPLC column (Bio-Rad) at a flow rate of 1 ml/min and 1 min fractions were collected. The chromatography buffer was the same as the incubation buffer except that BSA was omitted. 30 µl of fractions 19–29 were subjected to electrophoresis on a 16% Novex Tris-Glycine gel and Western analysis was performed as described above.

EXAMPLE 7

Calcineurin Phosphatase Assay

The calcineurin phosphatase assay is a modified version of previous assays (Liu, J., et al., *Cell*, 66, 807–815 (1991); Manalan, A., et al., *Proc. Natl. Acad. Sci. U.S.A.*, 80, 4291–4295 (1983)). Reaction mixtures (60 lad contained: 40 mM Tris (pH 8), 100 mM NaCl, 6 mM Mg(OAc)$_2$, 0.1 mM CaCl$_2$, 0.1 mg/ml BSA, 0.5 mM dithiothreitol, 190 nM bovine brain calmodulin (Sigma), 3 nM bovine brain calcineurin (Sigma), and 40 μM [$^{33}$P]RII peptide (Peptides International) (600 cpm/pmole). Reaction mixtures were pre-incubated for 30 min at 30° C. prior to addition of the labeled peptide. The reaction was initiated by addition of the peptide and the dephosphorylation reaction was allowed to proceed for 10 min at 30° C. The reaction was terminated by the addition of 0.5 ml of 5% trichloroacetic acid containing 100 mM sodium phosphate (stop buffer) and applied to a 0.5 ml Dowex 50W-X8, H$^+$ column. Free [$^{33}$P]phosphate was eluted from the column with 0.5 ml of stop buffer followed by 0.5 ml of water.

EXAMPLE 8

Peptide Synthesis, Purification, and Characterization

Peptides were synthesized by the Merrifield solid-phase technique on an Applied Biosystems 430A peptide synthesizer using standard Fmoc protected amino acids and the manufacturers suggested protocols for HBTU mediated couplings on p-benzyloxybenzyl alcohol resins. Peptides were simultaneously deprotected and cleaved from the resin with 90% trifluoroacetic acid (TFA), 5% thioanisol, 3% ethanedithiol, 2% anisole at room temperature for 2 hr. Crude peptides were precipitated with ethyl ether then dissolved in 10% acetic acid and lyophilized. The resulting crude peptides were purified by reverse-phase HPLC on Waters C18 Deltapak columns with a 45 min gradient of 5 to 50% acetonitrile in aqueous 0.1% TFA. Purity of the peptides was assessed by reversed phase HPLC on a Brownlee Spheri-5ODS column with a 45 min gradient of 5 to 50% acetonitrile in aqueous 0.1% TFA. All peptides were >95% pure. Molecular ions were obtained by ESI-MS to confirm the structure of each peptide.

EXAMPLE 9

Coupling Chemistry

Bovine thyroglobulin (33 moles) was dissolved in 2.5 ml of degassed 20 mM phosphate buffer (pH 8) and incubated with 10 μmoles Sulfo-MBS (Pierce) for 30 minutes at room temperature. The activated thyroglobulin coupling mixture was applied to a PD-10 column and the activated thyroglobulin was eluted with 3.5 ml of 50 mM phosphate buffer (pH 7) into a vial containing 6 μmoles of lyophilized peptide. The mixture was incubated overnight at 4° C. with gentle stirring and the peptide-thyroglobulin complex was separated from free peptide or reaction by-products by chromatography on a PD-10 column equilibrated with PBS. To determine the degree of coupling, 50 μl of the sample was hydrolyzed with 200 μl of 6 N HCl containing 0.1% phenol maintained at 110° C. in vacuo for 24 hrs. Amino acid analysis of the sample was performed using a Beckman Model 6300 amino acid analyzer.

EXAMPLE 10

Antiserum Production

New Zealand white rabbits were injected intramuscularly with 333 μg of immunogen conjugate in 1 ml of Freund's complete adjuvant. On days 7 and 35, rabbits were again injected with 333 μg of immunogen in Freund's complete adjuvant at 6–10 sites, subcutaneously. On day 45, the animals were bled, and boosted with the same amount of antigen. On day 55, animals were again boosted and 10 days later bled. This boosting and bleeding schedule was continued 3–5 times to obtain an adequate supply of antiserum. Serum was generated by clotting overnight and the serum was stored at −20° C.

EXAMPLE 11

FKBP12.6 Protein Sequencing

HPLC separations of Lys-C and chemical digests were performed on a Hewlett Packard 1090M system equipped with a UV diode array detector. Automated Edman degradations were performed on an Applied Biosystems Model 477A sequencer equipped with a Model 120A In-Line PTH analyzer. All chemicals and standards used for sequencing were purchased from Applied Biosystems. HPLC grade solvents used for peptide purification were purchased from EM Science. Sequencing grade endoproteinase Lys-C was from Promega. CNBr was from Pierce. Hydrogenated Triton X-100 was from CalBiochem. Sodium bicarbonate, 4-vinylpyridine, and 2-mercaptoethanol were from Sigma.

Enzymatic digestions were performed as previously described (Fernandez, J., et al., *Anal. Biochem.*, 201, 255–264 (1992)) with some modifications as follows. The blocking step with PVP-40 was omitted. Ponceau-stained FKBP12.6 PVDF protein bands (400 pmoles) were cut into 1×1 mm pieces and placed into an Eppendorf tube. The PVDF pieces were immersed in 50 μl of digestion buffer ( 100 mM NaHCO$_3$, 10% acetonitrile, 1% hydrogenated Triton X-100, pH 8.0). Sequencing grade endoproteinase Lys-C (1 μg) in 2 μl of 25 mM sodium phosphate (pH 7.5) and 1 mM EDTA was added to the tube. Digestion was performed overnight at 37° C. The peptides released in the supernatant were collected and the PVDF pieces were washed once with a 50 μl aliquot of digestion buffer. The combined supernatants (~100 μl) were put into a 1.5 ml Eppendorf tube and treated with 1 μl of a 10% 2-mercaptoethanol solution in water. The tube was incubated at 37° C. for 30 min. Then 1.5 μl of a 20% solution of 4-vinylpyridine in ethanol was added and the tube was incubated at room temperature for 30 min. The sample was then injected directly onto a Brownlee Aquapore C8 microbore column (1.0×250 mm) equilibrated in 0.1% TFA (solvent A). The column was washed for 20 minutes at 100 ml/min in solvent A. Peptides were eluted with a linear gradient (90 min) of 0% (100% solvent A) to 55% 0.08% TFA in acetonitrile/water (70:30 v/v) (solvent B) at a flow-rate of 50 μl/min. Peptide peaks were collected manually in 1.5 ml Eppendorf tubes.

The CNBr digestions were performed on both lyophilized FKBP12.6 and on FKBP12.6 blotted onto PVDF membranes by the separate methods outlined below. The lyophilized sample of FKBP12.6 (1500 pmoles) was dissolved in 50 μl of 70% formic acid. Approximately 40 μg of CNBr, freshly dissolved in 70% formic acid, was then added. The mixture was incubated for 24 hrs at room temperature in the dark. The mixture was diluted to 0.5 ml in water and dried in a Speed Vac. The sample was reconstituted in 25 μl of 25% trifluoroacetic acid and injected onto a Vydac C18 microbore column (1.0×250 mm) equilibrated in solvent A. A linear gradient of 0% to 100% solvent B was developed over a 60 min period at a flow rate of 50 μl/min. One peptide peak, CB2 (residues 30–66) was collected manually. It was not possible to isolate CB1 (residues 1–29) or CB3 (residues 67–107) by reverse phase HPLC.

To obtain the sequence of CB3, FKBP12.6 (400 pmoles)

was blotted onto a PVDF membrane and blocked with acetic anhydride in order to prevent the sequencing of peptide CB1 as follows. That portion of the PVDF membrane containing the FKBP12.6 protein was washed with methanol to remove water and air-dried. The membrane was then treated for 1 min at room temperature with 200 μl of methanol:trethylamine (3:1 v/v) in a 1.5 ml Eppendorf tube. Excess liquid was removed from the membrane and it was then incubated at room temperature in 200 μl of methanol:acetic anhydride (3:1 v/v) for 10 min. An equal volume of water was then added to remove excess acetic anhydride. The membrane was then washed four times in 1 ml of methanol:water (1:1 v/v) and allowed to air-dry prior to the in situ CNBr digestion. The PVDF membrane was cut into 1×1 mm pieces and placed on top of a polybrene pre-treated reaction cartridge filter at the bottom of a 10 ml beaker. The PVDF pieces and filter were soaked with 60 μl of a 70 mg/ml solution of CNBr in 70% formic acid. The beaker was sealed in parafilm and then in aluminum foil and the reaction allowed to proceed overnight at room temperature. The CNBr and formic acid were evaporated off with a stream of nitrogen. The PVDF pieces and reaction cartridge filter were then placed in the sequencer and CB2 and CB3 were sequenced together. The sequence of CB3 was obtained by subtraction of the CB2 sequence which was known from the solution CNBr digestion described above.

For chymotrypsin or trypsin cleavage of FKBP12.6, the protein was dissolved in 50 μl of 0.1M ammonium bicarbonate, pH 9.0. Chymotrypsin (Boehfinger Mannheim) was added at an enzyme:substrate ratio of 1:200 (w/w) and incubated for 18 hours at room temperature. The peptides were fractionated on an Applied Biosystems C4 column (2.1×100 mm) at a flow rate of 200 μl/min using a linear gradient of TFA-acetonitrile. Peaks were collected manually, adsorbed onto polybrene-impregnated PVDF strips, and loaded onto a modified Applied Biosystems 477A gas-phase sequencer equipped with a continuous-flow reactor as described (Shively, J., et al., *Anal. Biochem*, 163, 517–529(1989)).

EXAMPLE 12

Primer Preparation and Cloning of FKBP12.6 cDNA

In order to clone the complete cDNA encoding bovine brain FKBP12.6 we used Taq polymerase, to obtain from total bovine brain cDNA by PCR (polymerase chain reaction), a fragment of the cDNA encoding bovine brain FKBP12.6. We made use of the fact that Taq polymerase will not extend primers if the 3' ends are not annealed to the template. Therefore, the 3' ends of the PCR primers always encoded amino acids that were different between FKBP12 and FKBP12.6

Four sets of degenerate oligonucleotide primers (two sets of sense primers and two sets of antisense primers) were synthesized. We assumed that bovine brain FKBP12.6 had an initiator methionine.

The first set of actual sense primers is shown below. In the nucleotide sequences, N is (G,A,T, or C), Y is (T or C), R is (A or G), M is (A or C).

(SEQ ID NO:6): 5'-ATG GGN GTN GAR ATA GA-3'

(SEQ ID NO:7): 5'-ATG GGN GTN GAR ATC GA-3'

(SEQ ID NO:8): 5'-ATG GGN GTN GAR ATT GA-3'

The first set of antisense primers is shown below.

(SEQ ID NO:9): 3'-CAG CGN ATR CCN CGN TG-5'

(SEQ ID NO:10): 3'-CAA CGN ATR CCN CGN TG-5'

(SEQ ID NO:11): 3'-CAT CGN ATR CCN CGN TG-5'

(SEQ ID NO:12): 3'-CAC CGN ATR CCN CGN TG-5'

Each of the sense primers was 32-fold degenerate. Each of the antisense primers was 128-fold degenerate. They were used in all possible combinations (12) to PCR a fragment encoding bovine brain FKBP12.6 from 1 ng of total bovine brain cDNA.

The second set of sense primers were internal to the first set and are shown below.

(SEQ ID NO:13): 5'-MGN ACN TTY CCN AAG AA-3'

(SEQ ID NO:14): 5'-MGN ACN TTY CCN AAA AA-3'

The second set of antisense primers were internal to the first set and are shown below.

(SEQ ID NO:15): 3'-AG CTY CTY CCN CGN CG-5'

(SEQ ID NO:16): 3'-AA CTY CTY CCN CGN CG-5

The sense primers were 128-fold degenerate and the antisense primers are 64-fold degenerate. They were used in all possible combinations (four) with the twelve primary PCR reaction products. The total number of PCR reactions was 48.

A portion of each PCR reaction was subjected to agarose gel electrophoresis and only those reactions giving a product of about 150 bp were considered for further study. The PCR reactions yielding 150 bp products were all derived from the sense oligo:

(SEQ ID NO:13): 5'-MGN ACN TTY CCN AAG AA-3' shown above. An EcoRI-linkered version of that oligo was synthesized and used as the sense primer:

(SEQ ID NO:17): 5'-TGG AAC CTT GAA TTC MGN ACN TTY CCN AAG AA-3'

BamHI-linkered versions of the second set of antisense oligomers were synthesized and used as the antisense primer:

(SEQ ID NO:18): 3'-AAG CTY CTY CCN CGN CG CCT AGG TTC CAA TGG-5'

(SEQ ID NO:19): 3'-AAA CTY CTY CCN CGN CG CCT AGG TTC CAA TGG-5'

The PCR products were digested with EcoRI and BamHI to remove the ends and subcloned into EcoRI and BamHI digested pUC19. Transformants were sequenced. The sequence of the bovine brain FKBP12.6 cDNA encoding that portion of FKBP12.6 between the primers is relevant and is shown below (SEQ ID NO:20):

5'-GGC CAG ACG TGC GTG GTG CAC TAC ACA GGA ATG CTT CAA AAT GGC AAG AAA TTC GAT TCA TCC AGA GAC AGA AAC AAG CCT TTC AAG TTC AGA ATT GGC AAA CAG GAA GTC ATC AAG GGT-3'

That this sequence encodes FKBP12.6 and not FKBP12 was demonstrated by the fact that the translation product is that of bovine FKBP12.6 and not bovine FKBP12.

We used the primers described above on total human brain cDNA to find out if the same protein was expressed in humans. The PCR primers and methods used to isolate the human cDNA fragment were identical to the methods described above.

The human FKBP12.6 cDNA sequence of the region between the primers is shown below (SEQ ID NO:21):

```
5'-GGC CAA ACG TGT GTG GTG CAC TAC ACA GGA ATG
   CTC CAA AAT GGC AAG AAG TTT GAT TCA TCC AGA
   GAC AGA AAC AAA CCT TTC AAG TTC AGA ATT GGC
   AAA CAG GAA GTC ATC AAA GGT-3'
```

The amino acid sequence of the translation product of the isolated human cDNA is identical to that of the bovine sequence and different from that of human FKBP 12. Thus, human brain contains a protein encoding FKBP12.6.

EXAMPLE 13

Cloning of the FKBP12.,6 cDNA into E. coli Expression Vectors

Recombinant FKBP12.6 is produced in E. Coli following the transfer of the FKBP12.6 expression cassette into E. Coli expression vectors, including but not limited to, the pET series (Novagen). The pET vectors place FKBP12.6 expression under control of the tightly regulated bacteriophage T7 promoter. Following transfer of this construct into an E. Coli host which contains a chromosomal copy of the T7 RNA polymerase gene driven by the inducible lac promoter, expression of FKBP12.6 is induced when an appropriate lac substrate (IPTG) is added to the culture. The levels of expressed FKBP12.6 are determined by the assays described above.

The cDNA encoding the entire open reading frame for FKBP12.6 is inserted into the NdeI site of pET 11a. Constructs in the positive orientation are identified by sequence analysis and used to transform the expression host strain BL21. Transformants are then used to inoculate cultures for the production of FKBP12.6 protein. Cultures may be grown in M9 or ZB media, whose formulation is known to those skilled in the art. After growth to an approximate $OD_{600}$= 1.5, expression of FKBP12.6 is induced with 1 mM IPTG for 3 hours at 37° C. Authentic FKBP12.6 enzymatic activity may be found in the insoluble inclusion body fraction from these cells. Soluble FKBP12.6 is extracted from the inclusion body fraction with 5M guanidine-HCl in a buffer containing 50 mM Tris-HCl (pH 8) and 100 mM dithiothreitol. Active FKBP12.6 is generated from this extract following dialysis against 100 volumes of 25 mM HEPES (pH 7.5), 5 mM dithiothreitol, 10% sucrose.

EXAMPLE 14

In Vitro Translation of FKBP12.6 mRNA by Xenopus Oocyte Microinjection Vector and Expression in Mammalian Cells FKBP12.6 cDNA constructs are ligated into in vitro transcription vectors (the pGEM series, Promega) for the production of synthetic mRNAs.

Synthetic mRNA is produced in sufficient quantity in vitro by cloning double stranded DNA encoding FKBP12.6 mRNA into a plasmid vector containing a bacteriophage promoter, linearizing the plasmid vector containing the cloned FKBP12.6-encoding DNA, and transcribing the cloned DNA in vitro using a DNA-dependent RNA polymerase from a bacteriophage that specifically recognizes the bacteriophage promoter on the plasmid vector.

Various plasmid vectors are available containing a bacteriophage promoter recognized by a bacteriophage DNA-dependent RNA polymerase, including but not limited to plasmids pSP64, pSP65, pSP70, pSP71, pSP72, pSP73, pGEM-3Z, pGEM-4Z, pGEM-3Zf, pGEM-5Zf, pGEM-7Zf, pGEM-9Zf, and pGEM-11Zf, the entire series of plasmids is commercially available from Promega.

The double stranded FKBP12.6-encoding DNA is cloned into the bacteriophage promoter containing vector in the proper orientation using one or more of the available restriction endonuclease cloning sites on the vector which are convenient and appropriate for cloning FKBP12.6 DNA. The vector with the ligated FKBP12.6 DNA is used to transform bacteria, and clonal isolates are analyzed for the presence of the vector with the FKBP12.6 DNA in the proper orientation.

Once a vector containing the FKBP12.6-encoding DNA in the proper orientation is identified and isolated, it is linearized by cleavage with a restriction endonuclease at a site downstream from, and without disrupting, the FKBP12.6 transcription unit. The linearized plasmid is isolated and purified, and used as a template for in vitro transcription of FKBP12.6 mRNA.

The template DNA is then mixed with bacteriophage-specific DNA-dependent RNA polymerase in a reaction mixture which allows transcription of the DNA template forming FKBP12.6 mRNA. Several bacteriophage-specific DNA-dependent RNA polymerases are available, including but not limited to T3, T7, and SP6 RNA polymerase. The synthetic FKBP12.6 mRNA is then isolated and purified.

It may be advantageous to synthesize mRNA containing a 5' terminal cap structure and a 3' poly A tail to improve mRNA stability. A cap structure, or 7-methylguanosine, may be incorporated at the 5'terminus of the mRNA by simply adding 7-methylguanosine to the reaction mixture with the DNA template. The DNA-dependent RNA polymerase incorporates the cap structure at the 5' terminus as it synthesizes the mRNA. The poly A tail is found naturally occurring in many cDNAs but can be added to the 3' terminus of the mRNA by simply inserting a poly A tail-encoding DNA sequence at the 3' end of the DNA template.

The isolated and purified FKBP12.6 mRNA is translated using either a cell-free system, including but not limited to rabbit reticulocyte lysate and wheat germ extracts (both commercially available from Promega and New England Nuclear) or in a cell based system, including but not limited to microinjection into Xenopus oocytes, with microinjection into Xenopus oocytes being preferred.

Xenopus oocytes are microinjected with a sufficient amount of synthetic FKBP12.6 mRNA to produce FKBP12.6 protein. The microinjected oocytes are incubated to allow translation of the FKBP12.6 mRNA, forming FKBP12.6 protein.

These synthetic mRNAs are injected into Xenopus oocytes (stage 5–6) by standard procedures (Gurdon, J. B. and Wickens, M. D. *Methods in Enzymol.*, 101, 370–386 (1983)). Oocytes are harvested and analyzed for FKBP12.6 expression as described herein.

EXAMPLE 15 pcDNA-FKBP12.6 expression in Xenopus oocytes

Ooctyes are taken from adult females of *Xenopus laevis* using standard surgical procedure (Colman, A., 1984 In: Transcription and Translation—A Practical Approach, IRL Press). To remove follicle cells, oocytes are treated for 2–3 h with freshly made collagenase (2 mg/ml, type 2, Worthington Biochemical Corp., Freehold, N.J.) in $Ca^{2+}$-free ND96 solution (ND96 in mM: NaCl 96, KCl2, $MgCl_2$1, HEPES 5, Na-pyruvate 2.5, theophylline 0.5, gentamicin 50 mg/ml, + 1.8 $CaCl_2$, pH 7.6). Defolliculated stage 5-6 oocytes are selected and maintained in ND96 solution. Ooctye nuclei are injected with 1-5 ng of pcDNA-FKBP12.6 or pcDNA-FKBP12.6 (Bam) and then incubated at 18° C. for 48 h before challenge with agonist. Functional activity is determined by measurement of either agonist-induced $Ca^{2+}$-dependent $Cl^-$ current or light emission in oocytes injected with the $Ca^{2+}$-specific photoprotein aequorin (J. Blinks, Friday Harbor Photoproteins, WA), (Giladi and Spindel, *Biotechniques*, 10, 744–747 (1991). For the electrophysiological assays an ooctye is placed in a 0.5 ml perfusion chamber and voltage clamped at -60 mV (with microelectrodes of 0.5-2.0 M$\Omega$resistance filled with 3M CK1) using a Turbo TEC 01C amplifier (NPI Instruments, Germany). Ligand-containing solution is perfused and the current response is recorded. For the luminometric assay, aequorin-loaded oocytes (100 ng/ooctye) are placed individually in cuvettes containing 0.4 ml ND96 and the light emission provoked by ligand addition is recorded using a Bio-Orbit 1251 luminometer (Fisher Sci. Ltd.).

EXAMPLE 16

Cloning of FKBP12.6 cDNA into it Mammalian Expression Vector

FKBP12.6 cDNA expression cassettes are ligated at appropriate restriction endonuclease sites to the following vectors containing strong, universal mammalian promoters: pBC12BI (Cullen, B. R., *Methods in Enzymol.*, 152, 684–704 (1988), and pEE12 (CellTech EP 0,338,841) and its derivatives pSZ9016-1 and p9019. p9019 represents the construction of a mammalian expression vector containing the hCMVIE promoter, polylinker and SV40 polyA element with a selectable marker/amplification system comprised of a mutant gene for dihydrofolate reductase (mDHFR) (Simonsen, C. C. and Levinson, A.D., *Proc. Natl. Acad. Sci U.S.A.*, 80, 2495–2499 (1983)) driven by the SV40 early promoter. An SV40 polyadenylation sequence is generated by a PCR reaction defined by primers 13978-120 and 139778-121 using pD5 (Berker and Sharp, *Nucl. Acid Res.*, 13, 841–857 (1985)) as template. The resulting 0.25 Kb PCR product is digested with ClaI and SpeI and ligated into the 6.7 Kb fragment of pEE12 which has been likewise digested. The resultant plasmid is digested with BglII and SfiI to liberate the 3' portion of the SV40 early promoter and the GScDNA from the vector. A 0.73 Kb SfiI-XhoII fragment isolated from plasmid pFR400 (Simonsen, C. C. and Levinson, A. D., *Proc. Natl. Acad. Sci U.S.A.*, 80, 2495–2499 (1983)) is ligated to the 5.6 Kb vector described above, reconstituting the SV40 early promoter, and inserting the mdHFR gene. This plasmid is designated p9019. pSZ9016-1 is identical to p9019 except for the substitution of the HIV LTR for the huCMVIE promoter. This vector is constructed by digesting p9019 with XbaI and MluI to remove the huCMVIE promoter. The HIV LTR promoter, from residue -117 to +80 (as found in the vector pCD23 containing the portion of the HIV-1 LTR (Cullen, *Cell*, 46, 973 (1986)) is PCR amplified from the plasmid pCD23 using oligonucleotide primers which appended to the ends of the product the MluI and SpeI restriction sites on the 5' side while Hind III and Xba I sites are appended on the 3' side. Following the digestion of the resulting 0.2 kb PCR product with the enzymes MluI and Xba I the fragment is agarose gel-purified and ligated into the 4.3 Kb promotedess DNA fragment to generate the vector pSZ9016-1.

Cassettes containing the FKBP 12.6 cDNA in the positive orientation with respect to the promoter are ligated into appropriate restriction sites 3' of the promoter and identified by restriction site mapping and/or sequencing. These cDNA expression vectors are introduced into various host cells including, but not limited to: COS-7 (ATCC# CRL1651), CV-1 tat ((Sackevitz et al., *Science*, 238, 1575 (1987)), 293, L (ATCC# CRL6362)) by standard methods including but not limited to electroporation,or chemical procedures (cationic liposomes, DEAE dextran, calcium phosphate). Transfected cells and cell culture extracts can be harvested and analyzed for FKBP12.6 expression as described below.

All of the vectors used for mammalian transient expression may be used to establish stable cell lines expressing FKBP12.6. Unaltered FKBP12.6 cDNA constructs cloned into expression vectors will be expected to program host cells to make intracellular FKBP12.6 protein. The transfection host cells include, but are not limited to, CV- 1-P (Sackevitz et al., *Science*, 238, 1575 (1987)), tk-L (Wigler, et al. *Cell*, 11, 223 (1977)), NS/O, and dHFr- CHO (Kaufman and Sharp, *J. Mol, Biol.*, 159, 601 (1982)).

Co-transfection of any vector containing FKBP12.6 cDNA with a drug selection plasmid including, but not limited to G418, aminoglycoside phosphotransferase, pLNCX (Miller, A. D. and Rosman G. J., *Biotech News*, 7, 980–990 (1989)); hygromycin, hygromycin-B phosphotransferase, pLG90 (Gritz. L. and Davies, J., *Gene*, 25, 179 (1983)); APRT, xanthine-guanine phosphoribosyl-transferase, pMAM (Clontech) (Murray, et al., *Gene*, 31, 233 (1984)) will allow for the selection of stably transfected clones. Levels of FKBP12.6 are quantitated by the assays described above.

FKBP12.6 cDNA constructs are ligated into vectors containing amplifiable drug-resistance markers for the production of mammalian cell clones synthesizing the highest possible levels of FKBP12.6. Following introduction of these constructs into cells, clones containing the plasmid are selected with the appropriate agent, and isolation of an over-expressing clone with a high copy number of the plasmid is accomplished by selection in increasing doses of the agent. The following systems are utilized: the 9016 or the 9019 plasmid containing the mutant DHFR gene (Simonson, C. and Levinson, A., *Proc. Natl. Acad. Sci, U.S.A.*, 80, 2495 (1983)), transfected into DHFR-CHO cells and selected in methotrexate; the pEE12 plasmid containing the glutamine synthetase gene, transfected into NS/O cells and selected in methionine sulfoximine (CellTech, International Patent Application 2089/10404); and 9016 or other CMV promoter vectors, co-transfected with pDLAT-3 containing the thymidine kinase gene (Colbere and Garopin, F., *Proc. Natl. Acad, Sci.*, 76, 3755 (1979)) in APRT and TK deficient L cells, selected in APRT (0.05 mM azaserine, 0.1 mM adenine, 4 ug/ml adenosine) and amplified with HAT (100 uM hypoxanthine, 0.4 uM aminopterin, 16 uM thymidine).

EXAMPLE 17

Cloning of FKBP12.6 cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing FKBP12.6 cDNA is produced by the following standard methods (InVitrogen Maxbac Manual): the FKBP12.6 cDNA constructs are ligated downstream of the polyhedrin promoter in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA (Kitts, P. A., *Nuc. Acid. Res.*, 18, 5667 (1990)) into Sf9 cells. Recombinant pAC360 viruses are identified by the absence of inclusion bodies in infected cells (Summers, M. D. and Smith, G. E., *Texas Agriculture Exp. Station. Bulletin* No. 1555) and recombinant pBlueBac viruses are identified on the basis of β-galactosidase expression (Vialard, et al., *J. Virol.*, 64, 37–50 (1990). Following plaque purification and infection of sf9 cells with FKBP12.6 recombinant baculovirus, FKBP12.6 expression is measured by the assays described above.

The cDNA encoding the entire open reading frame for FKBP12.6 is inserted into the BamHI site of pBlueBacII. Constructs in the positive orientation with respect to the polyhedrin promoter are identified by sequence analysis and used to transfect Sf9 cells in the presence of linear AcNPV mild type DNA.

Authentic, active FKBP12.6 is found associated with the membranes of infected cells. Membrane preparations are prepared from infected cells by standard procedures.

EXAMPLE 18

Cloning of FKBP12.6 cDNA into Yeast Expression Vector

Recombinant FKBP12.6 is produced in the yeast *S. cerevisiae* following the insertion of the optimal FKBP12.6 cDNA construct into expression vectors designed to direct the intracellular expression of heterologous proteins. For intracellular expression, vectors such as EmBLyex4 or the like are ligated to the FKBP12.6 cistron (Rinas, U. et al., *Biotechnology*, 8, 543–545 (1990); Horowitz, B. et al., *J. Biol. Chem.*, 265, 4189–4192 (1989)). The levels of expressed FKBP12.6 are determined by the assays described above.

EXAMPLE 19

Purification of Recombinant FKBP 12.6

Recombinantly produced FKBP12.6 may be purified by antibody affinity chromatography. FKBP12.6 antibody affinity columns are made by adding the anti-FKBP12.6 antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized FKBP12.6 or FKBP12.6 subunits are slowly passed through the column. The column is then ished with phosphate-buffered saline together with detergents until the optical density falls to background, then the protein is eluted with 0.23M glycine-HCl (pH 2.6) together with detergents. The purified FKBP12.6 protein is then dialyzed against phosphate buffered saline.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, procedures other than the particular experimental procedures as set forth herein above may be applicable as a consequence of degeneracy and variations in the sequences of the proteins and DNA of the invention indicated above. Likewise, the characterization data observed may vary slightly according to and depending upon the particular assay or characterization method employed, and such expected variations or differences in the results are contemplated in accordance with the objects and practices of the present invention. It is intended, therefore, that the invention be defined by the scope of the claims which follow and that such claims be interpreted as broadly as is reasonable.

---

What is claimed is:

1. An isolated and purified homogeneous cytosolic binding protein, FKBP12.6, having a specific binding affinity for FK-506 and no specific binding affinity for cyclosporine A, and having a molecular weight in the range of 10–12 kilodaltons, comprising the N-terminal amino acid sequence (SEQ ID NO:1):

Gly Val Glu Ile Glu Thr Ile Ser Pro Gly Asp Gly Arg Thr Phe Pro
    Lys Lys Gly Gln Thr Cys Val Val His Tyr Thr Gly Met Leu
    Gln Asn Gly Lys Lys Phe Asp Ser Ser Arg Asp Arg Asn Lys
    Pro Phe Lys Phe Arg Ile Gly Lys Gln Glu Val Ile Lys Gly Phe
    Glu Glu Gly Ala Ala Gln Met Ser Leu Gly Gln Arg Ala Lys
    Leu Thr Cys Thr Pro Asp Val Ala Tyr Gly Ala Thr Gly His
    Pro Gly Val Ile Pro Pro Asn Ala Thr Leu Ile Phe Asp Val Glu
    Leu.

2. The FKBP12.6 protein of claim 1 immobilized on a support.

3. The FKBP12.6 protein of claim 1 immobilized on an affinity chromatography support.

* * * * *